US005326542A

United States Patent [19]

Sizer et al.

[11] Patent Number: 5,326,542

[45] Date of Patent: Jul. 5, 1994

[54] METHOD AND APPARATUS FOR STERILIZING CARTONS

[75] Inventors: Charles E. Sizer, Colleyville, Tex.; Terry D. Erickson; Terrence F. Manley, both of St. Paul, Minn.

[73] Assignee: Tetra Laval Holdings & Finance S.A., Pully, Switzerland

[21] Appl. No.: 955,259

[22] Filed: Oct. 1, 1992

[51] Int. Cl.[5] .................... A61L 2/10

[52] U.S. Cl. .................... 422/291; 422/302; 422/24; 422/22; 422/40; 422/41; 250/494.1; 99/451

[58] Field of Search .................... 422/24, 22, 302, 291, 422/20, 40, 41; 250/494.1, 461.2, 492.1; 426/248; 99/451, DIG. 14

[56] References Cited

U.S. PATENT DOCUMENTS

| | | | |
|---|---|---|---|
| 4,250,390 | 2/1981 | Nicholson | 250/494.1 |
| 4,289,728 | 9/1981 | Peel et al. | 422/24 |
| 4,366,125 | 12/1982 | Kodera et al. | 422/295 |
| 4,375,145 | 3/1983 | Mosse et al. | 53/425 |
| 4,900,934 | 2/1990 | Peeters et al. | 250/461.2 |
| 4,922,114 | 5/1990 | Boehme | 422/24 |
| 5,097,136 | 3/1992 | Meyer et al. | 250/492.1 |
| 5,124,130 | 6/1992 | Costello et al. | 422/82.06 |

OTHER PUBLICATIONS

"Surface Sterilization with Advanced UV Disinfection Systems", Aquionics Brochure.

"The Medium Pressure Arc Tube", Aquionics Information File IX.

"Effect of Chemical and Physical Sterilants on Aseptic Packaging of Dairy Products", Patil, et al., New Zealand Hournal of Dairy Science and Technology, vol. 23, pp. 175-183 (1988).

*Primary Examiner*—Robert J. Warden

*Assistant Examiner*—Hien Tran

*Attorney, Agent, or Firm*—Burns, Doane, Swecker & Mathis

[57] ABSTRACT

An ultraviolet (UV) sterilization system for food cartons is disclosed. An elongated UV lamp is mounted in a housing. A parabolic cylinder reflector is mounted in the housing with the focus of the reflector coinciding with the axis of the arc in the UV lamp. The shape of the parabolic reflector directs radiation from the lamp into cartons positioned on a conveyor below the lamp. The axis of the arc is parallel to the direction of movement of the cartons on the conveyor. The front surface of the reflector also absorbs heat from the lamp and heat is removed from the reflector by circulating air over the back surface of the reflector.

18 Claims, 6 Drawing Sheets

FIG. 1
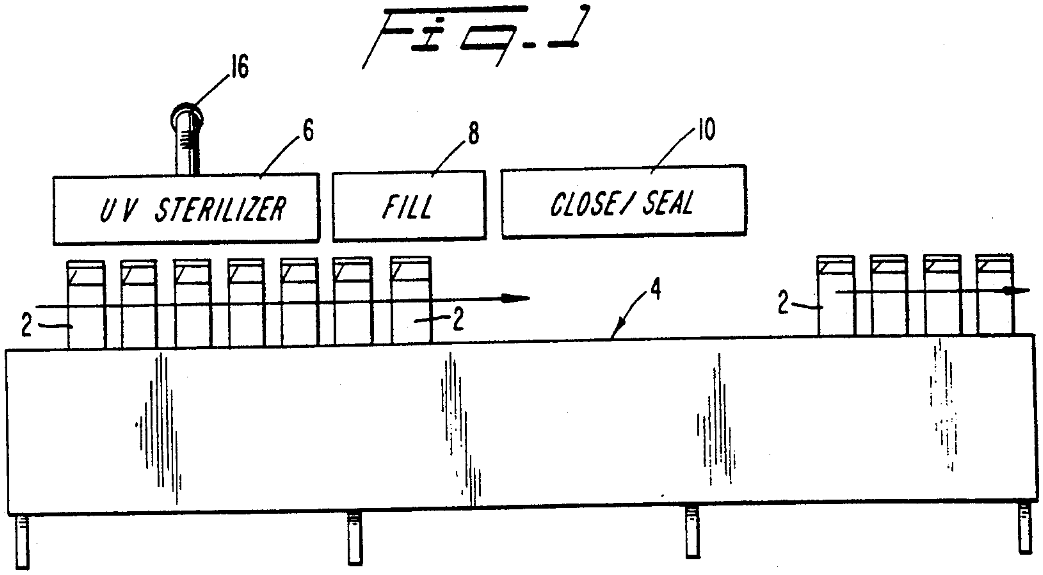
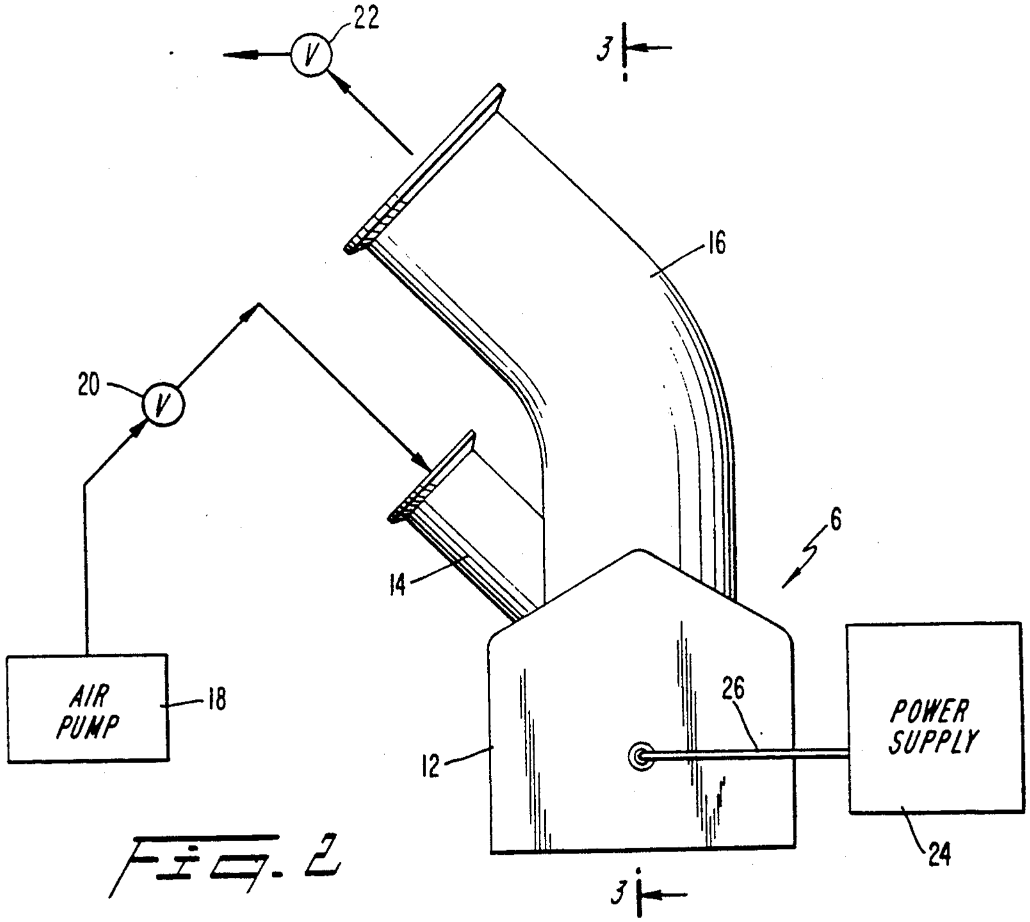
FIG. 2

12
36
42
48
30
62
58
2
66
4
40
16
14
50
52
46
34
56
60
44
28
38
32

6
16

14
12
28
34
54
52
40
42
62
44
50
62
60
46
46
90
92
94
2
6

METHOD AND APPARATUS FOR STERILIZING CARTONS

FIELD OF THE INVENTION

This invention relates to methods and apparatus for filling and sealing cartons with food products, and more particularly to methods and apparatus for sterilizing the interior of cartons prior to filling.

BACKGROUND OF THE INVENTION

Milk or juice is typically packaged in cartons that have been sterilized to prolong the shelf life of the contents under refrigeration. When milk or juice is packaged under aseptic packaging conditions, the contents are capable of being stored for a substantial period of time at room temperature without spoilage. Both of these packaging processes require effective sterilization of the interior of the carton before being filled.

Aseptic packages containing milk or juice may be stored at room temperature for substantial periods of time because the bacteria which normally produces spoilage has been killed in the packaging process. Various methods and apparatus have been developed for packaging milk and juice under aseptic conditions. For example, U.S. Pat. No. 4,375,145 discloses an aseptic packaging machine having a conveyor on which preformed cartons advance under ultraviolet germicidal lamps to expose the interior of the cartons to ultraviolet (UV) radiation. In addition, the interior of the cartons may be sprayed with a germicidal solution, such as hydrogen peroxide, before passing under the ultraviolet lamps.

The use of high intensity lamps necessitates incorporating a fast shuttering system for safety reasons and to prevent overheating of the cartons. During normal operation, the UV lamp is enclosed in the filling machine which prevents exposure of the operator to Uv light rays. If the filling machine jams or if for some reason the operator must open the doors to the filler, then there must be some mechanism to minimize exposure to the UV light. The UV light can be either turned off or shuttered. Turning off the light requires a lengthy start-up time whereas shuttering provides protection for the operator with no loss of time upon restarting.

U.S. Pat. No. 4,289,728 discloses a method for sterilization of the surfaces of food containers and other materials by applying a hydrogen peroxide solution, followed by ultraviolet radiation. This patent indicates that the peak intensity of ultraviolet radiation occurs at a wavelength of 254 nm. The concentration of the hydrogen peroxide solution is less than 10% by weight, and furthermore, the hydrogen peroxide solution is heated during or subsequent to irradiation.

Current technology utilizing ultraviolet (UV) sterilization of cartons is limited by the low intensity of the UV lamps that can be used. UV output in the range of 0.1 to 1 $W/cm^2$ has previously been considered to be a "high intensity" source for sterilization of packaging (Maunder, 1977). Low power lamps in the 0.1 to 1.0 $W/cm^2$ can be convection cooled and are effective in sterilizing flat surfaces in close proximity to the lamp.

Recent developments in the area of high output medium pressure mercury UV lamps have increased the light output to 50–250 Watts per inch of bulb length (17–85 $Watts/cm^2$). This type of lamp has a long cylindrical quartz glass tube containing medium pressure mercury vapor with electrodes at the opposite ends of the tube. The high power consumption of these lamps necessitates utilization of an active cooling system to prevent overheating of the lamp and to be able to restart the lamp after it has been temporarily shut down. Cooling systems generally consist of a thimble of quartz surrounding the lamp through which air or water is circulated.

UV sterilization has been shown to be suitable for sterilization of flat films but has limited applicability to preformed, angular containers (Maunder, 1977) due to the geometric and physical constraints associated with UV light. If a simple UV lamp is placed in close proximity above a preformed container, such as a gable top carton, the sterilization effectiveness is severely limited due to several reasons. The total light flux entering the carton is restricted to light that can be directed through the carton opening, which in the case of typical gable top cartons are 55×55 mm, 70×70 mm or 95×95 mm. Light emitted from a line source UV lamp decreases in intensity with the square of the distance from the light source. Thus, as the depth of the carton increases, the light intensity falls off dramatically.

Another problem in sterilizing these cartons with UV light is that the light enters the top of the carton and radiates toward the bottom substantially parallel to the sides of the carton. The germicidal effect of the light that impinges on the sides is very low because of the low angle of incidence. Thus, the sides of the cartons are the most difficult surfaces to sterilize, especially for tall cartons. When the cartons are positioned on the conveyor, two sides of the carton lie in a plane that is parallel to the axis of the lamp, while the other two sides are transverse to the axis of the lamp. Since the lamp is elongated, radiation impinges on the transverse sides of the carton at a higher angle of incidence than it does on the parallel sides of the carton. In the case of a single UV lamp source above the center of a 70×70×250 mm rectangular carton, the effective light intensity at the bottom of the carton would be reduced to 13.9% of the maximum intensity at that distance from the source. The carton sides transverse to the lamp axis receive light from the entire length of the bulb. Light originating from the lamp reflector on the side opposite the parallel carton wall will have a maximum incident angle and thus have an intensity equal to 27.0% of the lamp intensity.

A typical arrangement for a cylindrical UV light system has a single-mirrored lamp in a water-cooled sleeve placed in a shuttered, reflective housing. This arrangement is suitable for sterilization of flat surfaces and some shallow cartons but the intensity of the light falls rapidly with increasing distance from the bulb, so that it is not suitable for sterilizing tall cartons.

Although these prior methods and apparatus produce satisfactory results for flat films, they are neither effective nor efficient when used for sterilizing preformed cartons.

SUMMARY OF THE INVENTION

It is an object of this invention to substantially improve the efficiency and effectiveness of processes and apparatus for sterilizing the interior of preformed cartons prior to filling.

This object is accomplished in accordance with a preferred embodiment of the invention by utilizing an ultraviolet lamp which is cooled by radiation of heat to the cooled surface of an elongated semi-parabolic reflector. The shape of the semi-parabolic reflector and the location of the UV lamp in relation to the foci of the two parts of the parabolic reflectors provides UV radiation at the bottom of the carton that is substantially greater than previously achieved by prior methods and apparatus. The position of the UV lamp relative to the reflector and the flow of cooling air over the back of the reflector controls the operating temperature of the lamp, so that more effective surface sterilization is achieved.

An important feature of this invention is the use of double semi-parabolic reflectors to direct the ultraviolet light to the sides of the cartons. Positioning the ultraviolet arc of the lamp at the Foci of the semi-parabolic reflectors produces UV light which has a greater angle of incidence on the sides of the carton and a greater intensity of UV light at the sides and bottom of the carton.

The UV lamp is cooled with radiant cooling using the aluminum reflector as the heat sink for the lamp. Circulating air is used for cooling the back of the reflector in order to maintain a uniform reflector temperature which in turn maintains the temperature of the lamp. The aluminum surface efficiently reflects light of the germicidal wavelength and yet effectively absorbs sufficient radiant heat to cool the lamp. The cooling system provides a uniform temperature heat sink to maintain the lamp temperature substantially constant. Maintaining constant lamp temperature is necessary for maximum output of UV light, to minimize the restart-up time after an interruption in production, and to prolong the life of the lamp.

A water-cooled shutter is utilized to restrict the UV light flow from the lamp assembly whenever the conveyor jams or when the operator opens the doors to the filler. The shutter is required for safety reasons to prevent operator exposure to UV light and to prevent overheating of cartons which may be stopped directly under the lamp. Shuttering of the light increases the amount of heat which must be removed by the cooling system to prevent overheating of the lamp.

The excess heat is removed by the air cooling system and the water cooling of the shutter. If the stop is for a long duration, the lamp may be turned to half power to minimize the temperature build-up. From the half power setting, the light can be put back into production without a lengthy start-up period.

DESCRIPTION OF THE DRAWINGS

A preferred embodiment of the invention is illustrated in the accompanying drawings, in which:

FIG. 1 is a schematic view of a filling machine with the UV sterilizer in accordance with this invention;

FIG. 2 is an end elevational view of the UV sterilizer;

DETAILED DESCRIPTION

Figure 3:
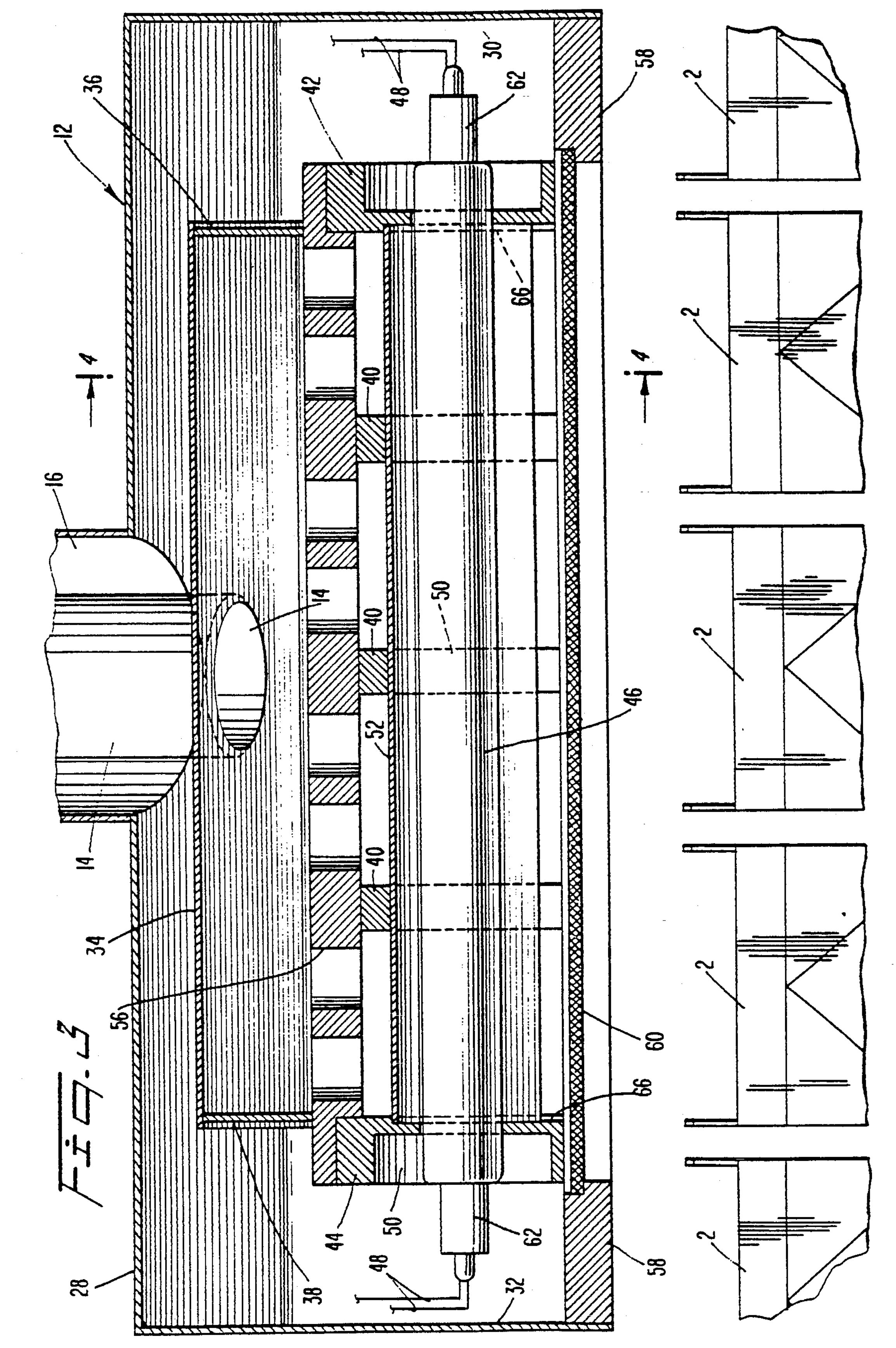
FIG. 3 is a cross-sectional view of the UV sterilizer along the line 3—3 in FIG. 2.

A common form of container for milk and juice is known as the gable-top container. The container has a paperboard substrate with a plastic coating on the inside and outside which enables the top of the carton to be closed and sealed in the shape of a gable top. Referring to FIG. 1, the cartons 2 typically have a square bottom which is heat sealed and placed on a conveyor 4 which advances stepwise to the right as viewed in FIG. 1. The cartons 2 are placed equidistant from each other and the cartons advance two positions during each periodic advancing step of the conveyor. Between each advancing step, the cartons remain stationary for processing.

The cartons first pass under an ultraviolet (UV) lamp assembly 6 which exposes the sides and bottom of the interior of the cartons 2 to ultraviolet light. At the next station, the cartons are filled by the filling mechanism 8. The cartons then pass through the closing and sealing station 10 where the top of the carton is closed. Heat is applied around the top of the carton, and the top then passes between clamping jaws which cause the top to be heat-sealed. The sealed cartons then pass off of the conveyor 4.

The UV lamp is preferably a medium pressure mercury vapor lamp. The lamp body is in the form of a quartz tube. The electrodes are sealed in the glass at each end of the tube. The tube is filled with an inert gas, such as argon. A small amount of mercury is placed in the tube. The operating pressure of a medium pressure arc tube is preferably between 100 and 10,000 torr. The lamp operates at a temperature of 1100° to 1500° F. When a high electric potential is applied between the electrodes, all of the mercury is vaporized and an arc is formed between the electrodes which produces ultraviolet radiation having wavelengths greater than 220 nanometers and preferably between about 240 nanometers to 370 nanometers. By limiting the radiation from the lamp to wavelengths greater than 220 nanometers, the formation of ozone is avoided. Lamps suitable for use in the apparatus of this invention are available commercially from Aquionics Inc. of Erlanger, Kentucky.

The lamp assembly 6 includes a housing 12 (FIG. 2) in which the UV lamp is mounted. The housing has an inlet pipe 14 and an outlet pipe 16 which communicate with the interior of the housing 12. An air pump 18 supplies air through a valve 20 to the inlet pipe 14, which causes the air to flow through the housing 12 and out through the outlet pipe 16 and through an exhaust valve 22. A suitable power supply 24 is provided for supplying power to the UV lamp through a cable 26.

Referring to FIG. 3, the housing 12 includes an outer shell 28 with opposite end walls 30 and 32. The outlet pipe 16 is secured in an opening at the center of the shell 28. An inner shell 34 having end walls 36 and 38 is mounted in the interior of the outer shell 28. The inlet pipe 14 passes through an opening in the outer shell 28 and is secured in an opening in the inner shell 34 to allow air to pass directly from the air pump 18 into the interior of the inner shell 34. The inlet pipe 14 also serves as a spacer for the shell 34 to provide the proper spacing between the inner shell 34 and the outer shell 28. A plurality of rib plates 40 are mounted in the inner housing 34 and at each end of the housing. End members 42 and 44 provide a mounting for the UV lamp tube 46 which extends between the two end members. As explained above, the lamp 46 has electrodes at each end which are supplied with electric current from the power supply 24 through insulated wires 48 at each end.

Figure 4:
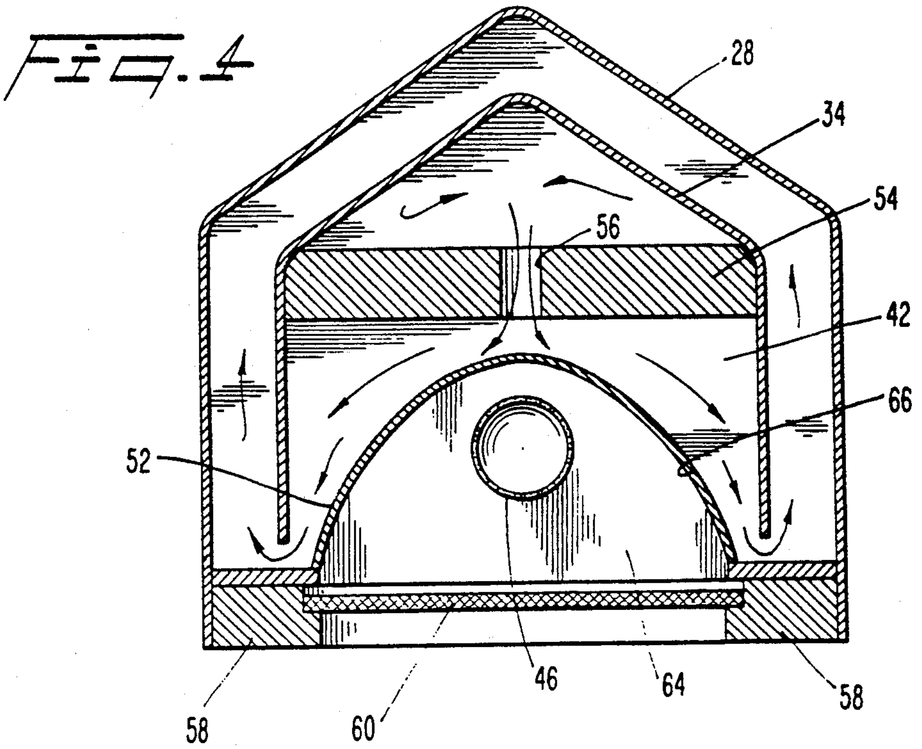
FIG. 4 is a cross-sectional view of the UV sterilizer along the line 4—4 in FIG. 3.

The rib plates 40 and the end members 42 and 44 have a concave recess 50 which supports a reflector 52. The opposite ends of the reflector 52 are received in the end members 42 and 44. As shown in FIG. 4, the rib plates 40 extend outwardly through slots in the sides of the inner shell 34 so that the opposite ends of the rib plates 40 engage the interior walls of the outer shell 28. A baffle plate 54 is secured to the rib plates 40 and to the end members 42 and 44. The baffle plate 54 has a plurality of slots 56 along the center line to allow air from the inlet pipe 14 to flow into the space between the reflector 52 and baffle plate 54.

The lower end of the shell 28 is closed by a mounting plate 58 in which a transparent quartz plate 60 is secured. The plate 60 is transparent to UV light in the range of 220 nanometers and higher. This spectral transmission band prevents ozone formation by the light. The mounting plate 58 has a central opening so that radiation from the UV lamp tube 46 is able to pass through the quartz plate 60 and into the cartons 2 which are positioned below the plate 60 (FIG. 3).

Figure 7:
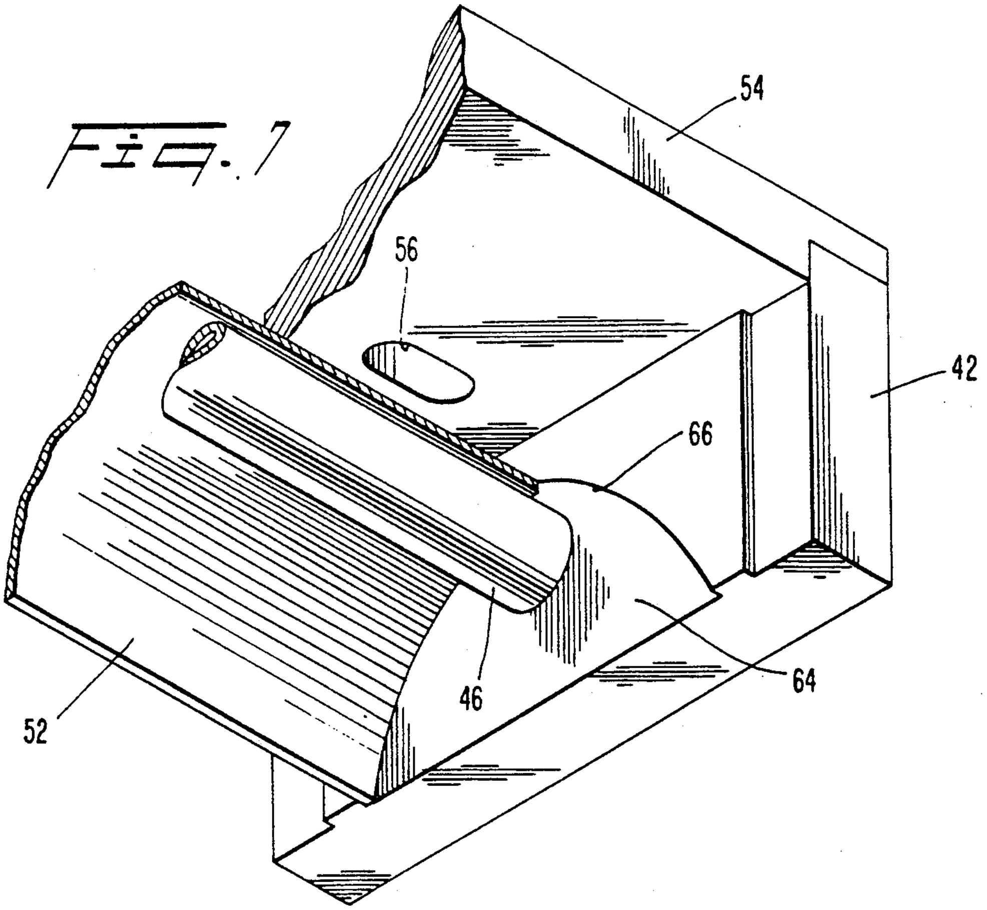
FIG. 7 is a detailed perspective view of the end plate and reflector assembly.

The UV lamp tube 46 is mounted in the end members 42, 44 in a position relative to the reflector 52 to provide optimum concentration of UV light to the interior of the cartons 2. As shown in FIG. 7 the end of the UV lamp tube 46 is mounted in a ceramic grommet 62 which extends through a hole in the end members 42 and 44.

The relationship of the reflector 52 and the UV lamp tube 46 comprise an important part of this invention. Semi-parabolic cylindrical reflectors having the light source at the focus reflects the UV energy parallel to the axis of the parabola. For a cylindrical bulb, a parabolic cylinder reflector would focus the light energy parallel to the axis of the parabola. With the reflector, the light intensity will diminish linearly with distance and thus would be much more satisfactory for sterilization at a distance from the bulb. Parabolic cylindrical reflectors must be designed with the lamp at or near the focus of the parabola in order to optimize the light beam. The design of such a reflector must take into account the geometric limitations due to the size of the bulb, the location of the bulb at the focus of the parabola and the shape of gable top cartons. The shape of the parabolic cylindrical reflector is defined by a parabola with the lamp at the focus. The equation of the parabola is $y=x^2/4a$ where "a" is the distance from the apex of the parabola to the focus. Thus, the bulb radius is the minimum value for a. A conventional medium pressure lamp with a cooling thimble of a 50 mm diameter would require at a minimum a parabolic reflector as shown in FIG. 3. The focal distance dictates the size of the parabola and results in a shape that is suboptimal for sterilization since the light is parallel to the sides of the container, most of the light is not focused down the carton and the beam is distorted by passing through the quartz cooling thimble which acts as a lens. To overcome these problems, it is necessary, in accordance with this invention, to decrease the focal distance and eliminate the cooling thimble surrounding the light.

Figure 8:
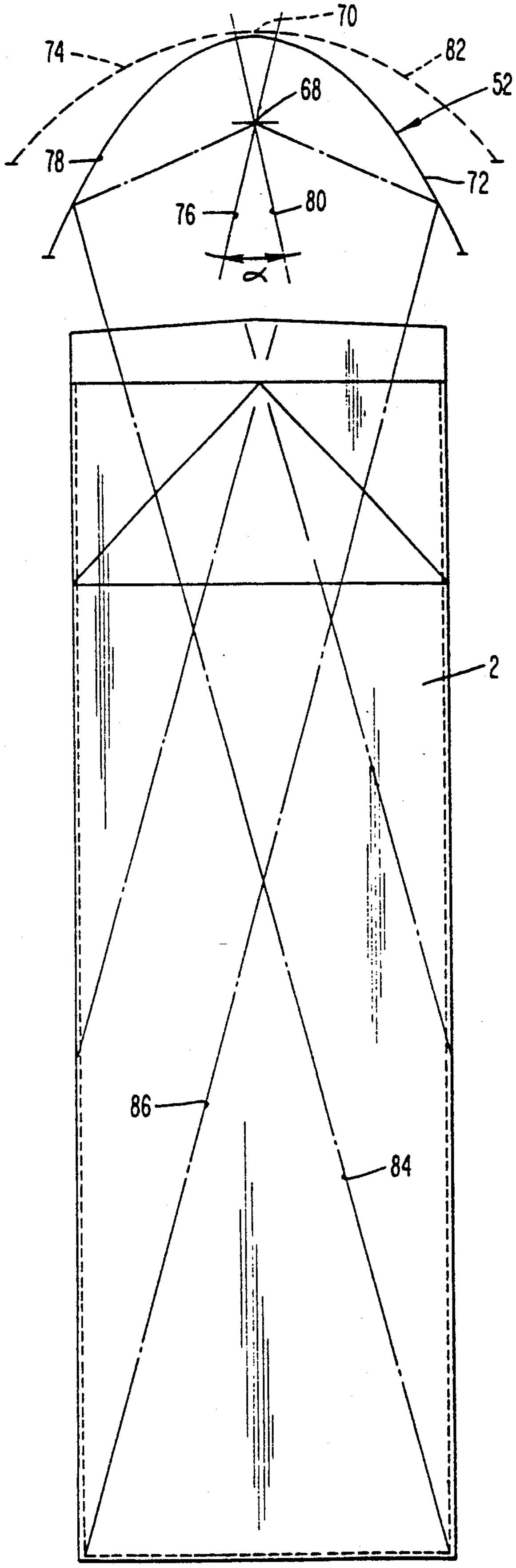
FIG. 8 is a schematic view of the lamp and reflector in relation to a carton.

As shown in FIG. 7, the reflector 52 is received in a recess 64 which has a curved edge 66 against which the outer surface of the reflector is seated. FIG. 8 is a schematic representation of the relationship between the lamp, the reflector and the carton that is to be sterilized. The UV lamp tube 46, when energized, has an arc that extends between the opposite ends of the UV lamp tube 46. Due to the heat generated by the arc, the center of the arc is displaced approximately 3 millimeters vertically upward relative to the center of the UV lamp tube. In FIG. 8, the center of the arc is represented at 68. The reflector 52 has the shape shown in solid lines in FIG. 8.

In a preferred embodiment, the distance between the apex 70 of the reflector 52 and the center of the arc 68 is 15.5 millimeters. The reflector 52 has a parabolic shape which is defined by the formula $y=x^2/4a$, where a is the distance between the center of the arc 68 and the apex 70 of the parabola. The reflector 52 actually comprises two parabolic curves which have a common focus at the center of the arc 68. The right side of the reflector 52 which is designated 72 in FIG. 8 would have, if continued beyond the apex 70, the shape 74 shown in dotted lines and a central axis 76. The left side 78 of the reflector 52 has a parabolic shape with a central axis 80. The virtual continuation 82 of the left side 78 is shown in dotted lines in FIG. 8. The parabolic shape of the reflector 52 is therefore a compound of the two sides 72 and 78 which in the case of an imperial quart carton (70 mm×70 mm×240 mm) are rotated through 13 degrees from the vertical so that the angle $\alpha$ between the axes 76 and 80 is 26 degrees. The angle of rotation for the parabolic reflectors would be determined for each carton size by the maximum angle of incidence allowed by the geometry of the cartons in relation to the lamp. The apex 70 of the reflector 52 is shaped to blend the two sides 72 and 78 in a continuous curve. In rotating the sides 72 and 78, it is important that the focus of both sides remains at the same position 68.

The characteristic of a parabola is that light emitted from the center of the arc 68 that impinges on the parabolic surface is reflected in a direction which is parallel to the central axis. As can be seen in FIG. 8, the lines 84 and 86 represent reflected radiation from the center of the arc 68 which reaches the bottom of the carton 2. The lines 84 and 86 are parallel to the central axes 80 and 76, respectively. The height of the carton that can be used with a particular filling machine may vary according to the volume of the cartons being filled. The taller cartons, such as the 1 quart, 1 liter or ½ gallon containers, have a sufficient height that UV light sterilization has been a problem. It is particularly important that the UV light impinge on the side walls of the carton at the maximum angle permitted by the geometry of the carton and the reflector. It has been determined that, for an imperial quart carton (70 mm×70 mm×240 mm), the angle of incidence should be 13 degrees or greater in order to achieve optimum effect from the UV light. For containers having a height-to-width ratio that is equal to or greater than 2.0, the lamp arrangement of this invention achieves significant improvement in sterilization.

An important feature of this invention is the arrangement of the parabolic reflector around the UV lamp tube. In a conventional installation, the tube normally operates at a temperature of 1100 degrees to 1500 degrees F., and in order to protect the tube and the reflector, the UV lamp is enclosed within a protective quartz sleeve and cooling media, such as water or air, is circulated outside the protective sleeve. It has been discovered that if the protective sleeve is removed, the amount of light captured by the parabolic reflector can be increased and scattering of the light by the protective sleeve is eliminated. By removing the sleeve, the parabolic reflector can be designed to collect the largest amount of light from the bulb by placing the focal point closer to the reflector yielding a deep parabola. The deep parabola captures about 270 degrees of the light output and simultaneously directs it into the regions of the carton which are most difficult to sterilize. In accordance with this invention, the UV lamp is cooled by radiant heat transfer utilizing an air-cooled reflector as a heat sink. Furthermore, when hydrogen peroxide is present in the carton, the UV light produces radicals of hydrogen peroxide which enhance the killing effect of the UV. If hydrogen peroxide is not present, then UV light having a wavelength in the region of 220–300 nm produces an effective germicidal action.

Another feature of this invention is the use of radiant heat transfer to maintain the lamp at the proper temperature. The aluminum reflector is used both to reflect the UV wavelength light and simultaneously absorb heat of other wavelengths to maintain the proper lamp temperature. The reflector temperature can be regulated by controlling the amount of air being passed over the reflector and is monitored by a thermocouple at the air outlet. The reflector temperature is kept uniform by introducing the cold air at the hottest position which is the point directly above the lamp. The air then flows over the rest of the reflector which helps maintain a uniform distribution over the entire surface of the reflector. By maintaining a constant temperature of the housing in the range of 50–100 degrees C., the lamp may be run continuously and is prevented from overheating. Furthermore, the sterilization may be interrupted by either shuttering the lamp or by turning off the lamp.

Figure 5:
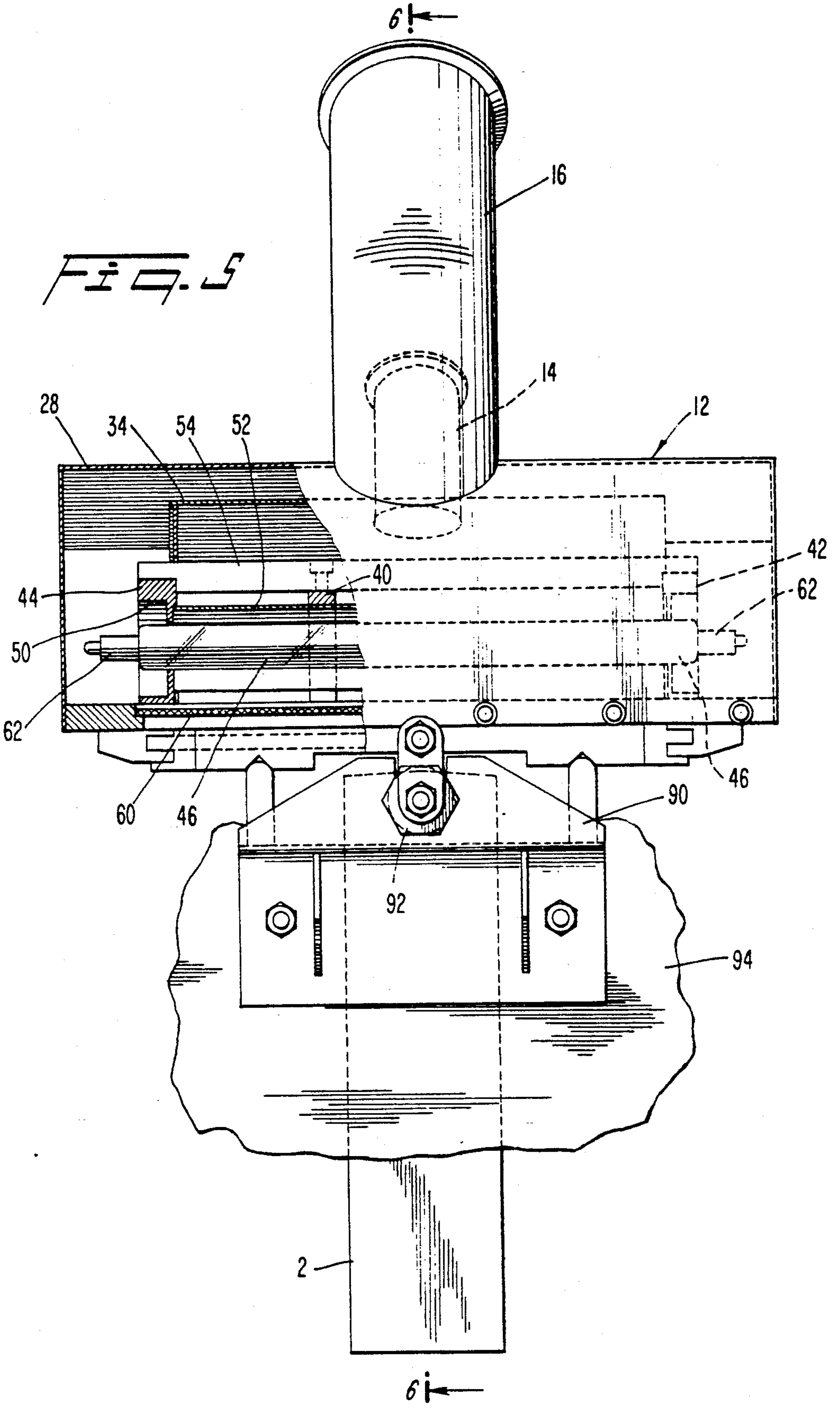
FIG. 5 is a top plan view partially in cross-section of the UV sterilizer.
Figure 6:
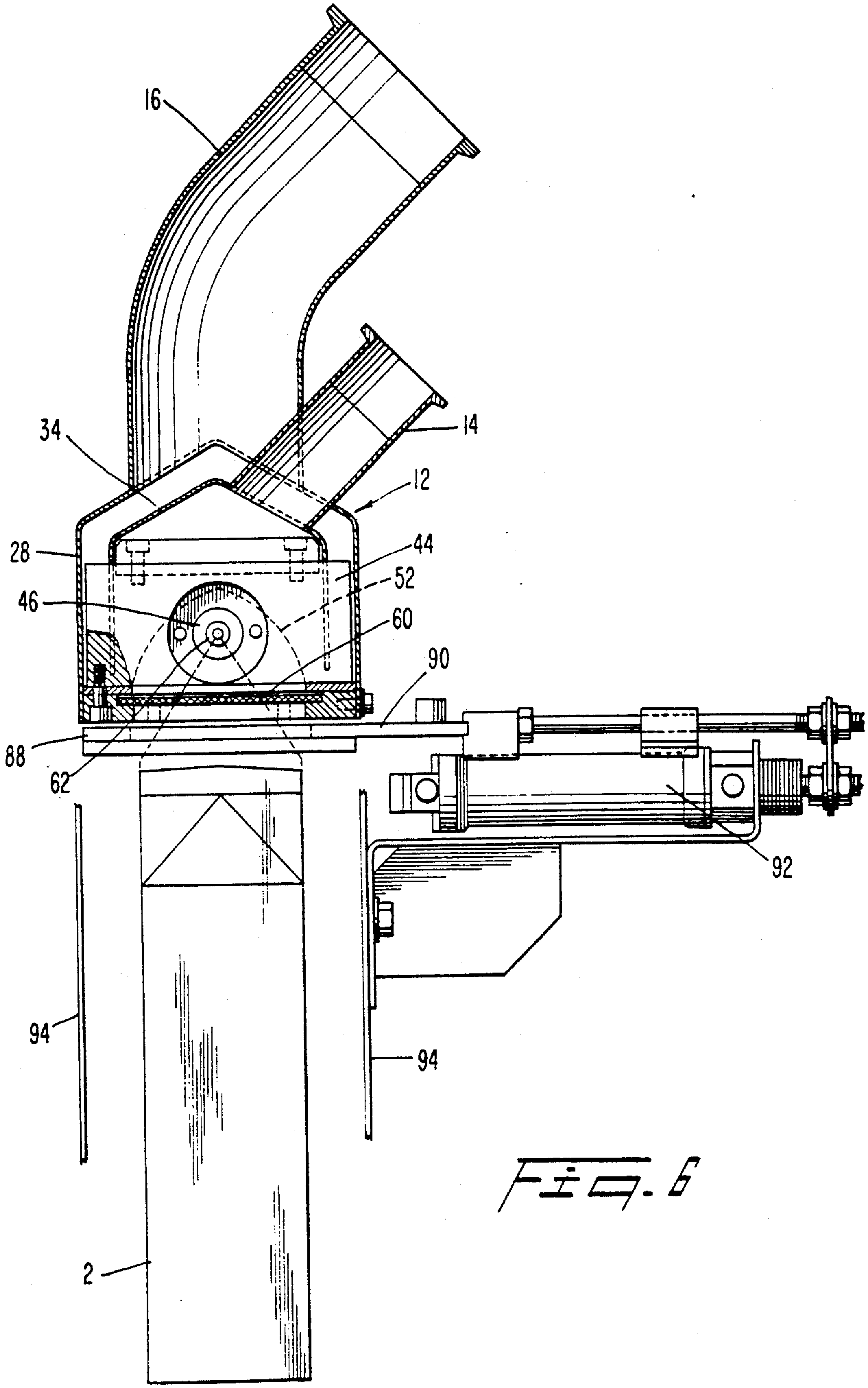
FIG. 6 is a cross-sectional view of the UV sterilizer along the line 6—6 in FIG. 5.

In order to protect the workers and to prevent damage to the cartons in the event it is necessary to stop the sterilization process temporarily, a shutter assembly is provided. As shown in FIGS. 5 and 6, the housing 12 has a transverse slot 88 for receiving a shutter plate 90. The shutter plate 90 is mounted for reciprocating movement by means of a power cylinder 92 which is mounted on the machine frame. By means of suitable controls, the cylinder 92 may be actuated to cause the plate 90 to move toward the left as viewed in FIG. 6 to block radiation from the housing 12. As a further safeguard, panels 94 may be mounted on opposite sides of the housing. The generation of heat may also be reduced by reducing the power to the lamp by about one-half. This will allow the lamp to be put back into production without a lengthy start-up period.

While this invention has been illustrated and described in accordance with a preferred embodiment, it is recognized that variations and changes may be made without departing from the invention as set forth in the claims.

What is claimed is:

1. Apparatus for sterilizing the interior of food cartons of the type having a bottom and upright side walls, the apparatus comprising:

(a) conveyor means for supporting and advancing a plurality of cartons along a path;

(b) a source of ultraviolet light, said source of ultraviolet light being elongated and having a longitudinal axis, said path being substantially parallel to said axis;

(c) a relfector extending along said longitudinal axis and spaced from said source of ultraviolet light for reflecting light from said source of ultraviolet light toward a bottom and side walls of cartons on said conveyor means, said reflector being elongated and being transversely curved about said longitudinal axis, said reflector having opposite parabolic sides joined together along an apex parallel to said longitudinal axis, said sides being rotated from the vertical about 13 degrees toward each other and having a common focus at the source ultraviolet light;

(d) cooling means for cooling said reflector means; and (e) power means for operating said source of ultraviolet light.

2. The apparatus according to claim 1 including shutter means for selectively blocking radiation from said source of ultraviolet light.

3. The apparatus according to claim 1 wherein said reflector has an inside surface and an outside surface, said inside surface being exposed to said source of ultraviolet light, said cooling means including fluid circulating means for contacting the outside surface of the reflector with a cooling fluid to maintain the reflector at a predetermined temperature.

4. The apparatus according to claim 3 wherein the reflector is formed of aluminum sheet.

5. Apparatus for sterilizing the interior of food cartons of the type having a bottom and upright side walls, the apparatus comprising:

(a) conveyor means for supporting a plurality of cartons along a predetermined straight path;

(b) housing means spaced above said conveyor means;

(c) an ultraviolet lamp having an elongated tube and electrodes at opposite ends, said tube having a central axis that is substantially parallel to said straight path;

(d) means for mounting said ultraviolet lamp in said housing means; said housing means including a parabolic reflector extending along one side of said elongated tube opposite said conveyor, said reflector being spaced from said elongated tube and being shaped to focus light from the ultraviolet lamp toward a bottom and side walls of cartons on said conveyor means; said parabolic reflector having opposite sides joined together along an axis parallel to said central axis, said reflector sides being rotated from the vertical about 13 degrees toward each other (e) means for circulating a cooling fluid through said housing means to remove heat from said reflector.

6. The apparatus according to claim 5 wherein said housing means includes shutter means for selectively blocking radiation from said ultraviolet lamp.

7. The apparatus according to claim 5 wherein said means for mounting said ultraviolet lamp includes a pair of end members, said elongated tube is received in said pair of end members, said reflector is formed of an impervious sheet material and is received in said pair of end members, said housing means includes a transparent plate extending between said pair of end members, wherein said reflector and said pair of end members and said transparent plate form an enclosure for the ultraviolet lamp.

8. The apparatus according to claim 7 wherein the transparent plate transmits only light having a wavelength greater than 220 nanometer.

9. The apparatus according to claim 7 wherein said sheet material is aluminum.

10. The apparatus according to claim 5 wherein said means for mounting said ultraviolet lamp includes a pair of end members, said elongated tube is received in said pair of end members, said reflector is formed of a gas impervious sheet material and is received in said end members.

11. The apparatus according to claim 10 wherein said housing includes baffle means in said housing and spaced from the reflector, said baffle means having a plurality of openings, said means for circulating includes a gas inlet passage, said baffle means being positioned between said gas inlet passage and said reflector for distributing gas along the length of said reflector.

12. The apparatus according to claim 11 wherein said housing includes shell means extending along said tube, said means for circulating gas including a gas outlet passage, said shell means being positioned to allow passage of gas to flow from adjacent to said opposite longitudinal sides of the reflector to said gas outlet passage.

13. The apparatus according to claim 12 wherein said gas inlet passage and said gas outlet passage are positioned midway of the length of said tube.

14. Apparatus for sterilizing the interior of food cartons of the type having a bottom and upright side walls, the apparatus comprising:

(a) conveyor means for supporting a series of cartons on a support surface that advances along a predetermined straight path;

(b) housing means spaced above said conveyor means, said housing means including an outer shell and an inner shell, said outer shell and said inner shell each having end walls, said end walls of said inner shell being spaced from said end walls of said outer shell;

(c) a pair of end members mounted in the respective end walls of said inner shell, an ultraviolet lamp in the form of an elongated tube having opposite ends and electrodes at the opposite ends of the tube, said tube having a central axis that is substantially parallel to said straight path, the opposite pair of ends of said tube being mounted in said end members, said ultraviolet lamp when energized produces an arc of radiation; and (d) an elongated reflector extending along said tube, said reflector being mounted in said inner shell to prevent fluid communication between an exterior of said tube and an interior of both of said shells, said reflector having first and second parabolic reflectors, said first and second parabolic reflectors each having a central axis and a focus, said first parabolic reflector having a central axis that intersects the central axis of the second parabolic reflector at an acute angle and the focus of the first and second parabolic reflectors coincide with said arc of radiation.

15. The apparatus of claim 14 wherein said reflector is formed of a sheet of aluminum.

16. The apparatus according to claim 14 wherein said acute angle is about 26 degrees.

17. The apparatus according to claim 14 wherein said first and second parabolic reflector are joined together along an apex.

18. The apparatus according to claim 14 wherein said ultraviolet lamp is a medium pressure mercury vapor lamp.

* * * * *